United States Patent [19]

Derez et al.

[11] Patent Number: 4,916,064

[45] Date of Patent: Apr. 10, 1990

[54] CARBOHYDRATE REFINING PROCESS AND NOVEL ENZYME COMPOSITIONS SUITABLE FOR USE THEREIN

[75] Inventors: Frank G. H. Derez, Halle; Jos W. G. C. de Sadeleer, Kessel Lo; Alan L. Reeve, Leefdaal, all of Belgium

[73] Assignee: CPC International Inc., Englewood Cliffs, N.J.

[21] Appl. No.: 915,438

[22] Filed: Oct. 6, 1986

[30] Foreign Application Priority Data

Oct. 10, 1985 [GB] United Kingdom ............... 8525012

[51] Int. Cl.$^4$ .............................................. C12P 19/14
[52] U.S. Cl. ....................................... 435/99; 127/29; 127/30; 426/658; 426/661; 435/183; 435/198; 435/262; 435/274; 435/275; 435/917
[58] Field of Search ............... 435/274, 275, 183, 198, 435/917, 262, 99; 127/29, 30; 426/658, 661

[56] References Cited

U.S. PATENT DOCUMENTS

| | | | |
|---|---|---|---|
| 2,970,086 | 1/1961 | Kerr | 435/917 |
| 3,264,193 | 8/1966 | Kool et al. | 435/917 |
| 3,901,763 | 8/1975 | Horiuchi et al. | 435/196 |
| 4,200,692 | 4/1980 | Puls et al. | 435/99 |
| 4,298,400 | 11/1981 | Armbruster | 127/29 |
| 4,562,150 | 12/1985 | Yamanobe et al. | 435/99 |
| 4,612,284 | 9/1986 | Pickens et al. | 435/99 |
| 4,636,468 | 1/1987 | Arbige et al. | 435/198 |

FOREIGN PATENT DOCUMENTS

| | | |
|---|---|---|
| 0039962 | 11/1981 | European Pat. Off. . |
| 0078556 | 5/1983 | European Pat. Off. . |
| 0078621 | 5/1983 | European Pat. Off. . |
| 2065689 | 7/1981 | United Kingdom . |
| 2085904 | 5/1982 | United Kingdom . |

OTHER PUBLICATIONS

Karkalas, J., "Modern Methods of Purification of Starch Hydrolyzates", *Die Starke*, 19, No. 10, pp. 338–345 (1967).

*Primary Examiner*—Robert Wax

[57] ABSTRACT

A process is provided for treating aqueous carbohydrate solutions with phospholipase enzyme compositions to improve the filterability and clarity of the filtrate of such solutions.

11 Claims, No Drawings

CARBOHYDRATE REFINING PROCESS AND NOVEL ENZYME COMPOSITIONS SUITABLE FOR USE THEREIN

FIELD OF THE INVENTION

The present invention relates to an improved process for refining certain aqueous solutions of carbohydrate origin, to a process for improving in particular the filterability of a starch hydrolysate, especially a wheat starch hydrolysate, to improvements in the clarity of the filtrate thereby obtained and to enzyme compositions suitable for achieving such improvements.

BACKGROUND OF THE INVENTION

Aqueous solutions of carbohydrate origin are encountered widely in industry in which naturally-occurring carbohydrate-containing materials are processed to give useful products. Examples of such processes include industrial reactions in which carbohydrates are broken down enzymatically or analogous processes in which the breakdown takes place by chemical action. The products of such processes are often obtained in the form of aqueous solutions comprising suspended by-product material which is separated by filtration. Problems are frequently encountered in such filtrations and it is often difficult to obtain a filtrate free from cloudiness. We have now found that the problems are often caused by the presence in the aqueous solutions of certain phosphorus-containing compounds and the present invention comprises a process for dealing with such compounds so that the filterability of the aqueous solutions is improved.

We have found in particular that the process of the invention is applicable to solutions in which the carbohydrate is starch which has been subjected to a hydrolytic process. For reasons of convenience, the process of the invention will be described subsequently in this specification in terms of starch although it should be borne in mind that the process and process conditions are applicable to aqueous solutions derived from other carbohydrates.

Starch is a high polymer carbohydrate made up of glucopyranose units joined together by alpha-glucosidic linkages. The polymer may be broken down by hydrolysis to yield lower molecular weight oligosaccharides and ultimately the monomer unit, glucose. The hydrolysis may be catalysed by acids or by enzymes, acids and alpha-amylases causing a more or less random cleavage of the starch molecule by hydrolysing the alpha-D-(1->4) glucosidic bonds. Beta-amylases are more specific in their action, splitting-off maltose directly from the starch or oligosaccharide molecule while glucoamylases are capable of splitting-off D-glucose (dextrose). Debranching enzymes, e.g., pullulanase, may also be used to facilitate the hydrolysis of the amylopectin starch component.

The so-called starch syrups are starch hydrolysates which are produced from starch by acid and/or enzymatic hydrolysis and which generally contain dextrose and/or maltose with trimers and other oligomers up to DP 20 or even higher ("DP" is "degree of polymerisation" and is followed by a digit(s) indicating the number of monomer units in the molecule). The hydrolysates have a range of compositions and a variety of uses many of which require the syrup to be clear and almost colorless.

We have encountered problems in the production of such syrups, particularly from wheat starch, finding that the hydrolysis product is very difficult to filter using standard equipment and that the filtrate is unacceptably cloudy. We have found, following an extensive investigation, that the problem is caused by the presence of phospholipids and that the filtration rate and clarity of a starch hydrolysate may be improved by treatment with certain enzymes.

SUMMARY OF THE INVENTION

According to the invention therefore a process for the treatment of an aqueous solution of carbohydrate origin which is difficult to filter and/or which produces a cloudy filtrate, is characterised in that the solution contains as impurity a phospholipid and is treated before filtration under conditions such that the filterability of the solution and/or the clarity of the filtrate are improved by contact with an enzyme composition containing a phospholipase enzyme, the ratio of phospholipase enzyme to total xylanase and beta-glucanase enzymes which may be present being at least 0.05:1, preferably at least 1:1, more preferably at least 5:1, and particularly at least 10:1.

Further provided in accordance with this invention is an enzyme composition suitable for the treatment of an aqueous solution of carbohydrate origin which contains as impurity a phospholipid, said enzyme composition comprising in an amount of at least 5000 units/gram total protein of the enzyme composition and in which the ratio of phospholipase enzyme to total xylanase and beta-glucanase which may be present is at least 0.05:1, preferably at least 1:1, more preferably at least 5:1, and particularly at least 10:1.

DETAILED DESCRIPTION OF THE INVENTION

Satisfactory enzyme compositions for use in the process contain a phospholipase and a xylanase and/or beta-glucanase in which the ratio of phospholipase to total xylanase and beta-glucanase lies in the range 0.05:1 to 50:1, particularly 1:1 to 30:1.

It is preferred that the enzyme composition used in the process contains at least 5000 units phospholipase/gram total protein, preferably 15,000 units/gram, more preferably 50,000 units/gram, particularly 100,000 units/gram total protein.

Phospholipase enzymes are enzymes which catalyse the hydrolysis of phospholipids. Phospholipids may be considered as derivatives of glycerophosphate in which the two hydroxyls are esterified by long-chain fatty acids and the phosphoryl group forms a phosphodiester bond with a polar moiety.

All four ester moieties in a phospholipid are susceptible to enzymatic hydrolysis. A phospholipase that cleaves the acyl ester at the sn-1 position is designated a phospholipase $A_1$, and one that cleaves at the sn-2 position is designated a phospholipase $A_2$. An enzyme that cleaves the phosphodiester bond on the glycerol side is designated a phospholipase C, and on the polar side a phospholipase D. Enzymes that hydrolyze the remaining acyl group on a lysophospholipid, i.e., a partially-hydrolysed phospholipid, carry out the same type of reaction as phospholipase $A_1$ or $A_2$ and are designated here as phospholipase $L_1$ or $L_2$. The latter enzymes are commonly referred to as lysophospholipases. The points of cleavage are shown schematically as follows:

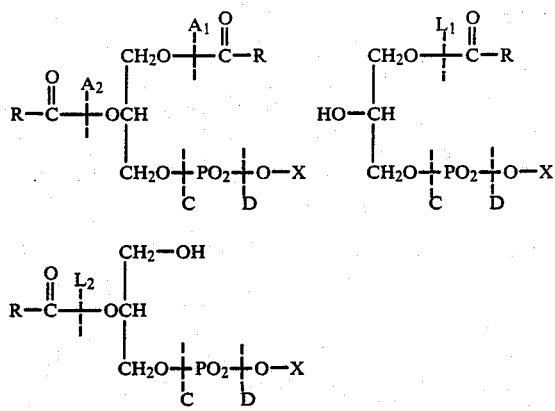

The phospholipase enzymes which are useful in the process of the invention are those designated $A_1$, $A_2$, $L_1$, $L_2$ and C. Some $A_1$ and $A_2$ enzymes also have $L_2$ and $L_1$ activity respectively. If they do not, it may be necessary to use a combination of $A_1+L_2$ or $A_2+L_1$ enzymes. For the application to wheat starch hydrolysates, for which the process of the invention is particularly suitable, a phospholipase possessing $L_1$, $L_2$ or C activity is necessary, a phospholipase $L_1$ or $L_2$ being preferred.

The Commission on Enzymes of the International Union of Biochemistry (1961) defines a standard unit of any enzyme as that amount which will catalyse the transformation of one micromole of a specified substrate per minute under prescribed conditions, i.e., temperature, pH, nature of the substrate. The phospholipase content of a given enzyme sample may be determined by following with NMR the disappearance of lecithin or lysolecithin in a standard solution containing a known amount of the enzyme. Other methods of determination are described later in this specification.

Another aspect of the invention concerns the provision of an enzyme composition suitable for use in the process of the invention and which comprises a phospholipase which is present in an amount of at least 5000 units/gram total protein of the enzyme composition and in which the ratio of phospholipase enzyme to total xylanase and beta-glucanase which may be present is at least 0.05:1, preferably at least 1:1, more preferably at least 5:1, and particularly at least 10:1.

Satisfactory enzyme compositions contain a phospholipase and a xylanase and/or beta-glucanase in which the ratio of phospholipase to total xylanase and beta-glucanase lies in the range 0.05:1 to 50:1, particularly 1:1 to 30:1.

It is preferred that the enzyme composition contains at least 15,000 units phospholipase/gram total protein, preferably 50,000 units/gram, particularly 100,000 units/gram total protein.

The enzyme composition is suitably of microbial origin and preferably contains more phospholipase $A_1$, $A_2$, $L_1$, and/or $L_2$ than phospholipase C. The microorganisms which may be used to produce the phospholipase composition according to the invention include *Aspergillus*, e.g., *Aspergillus niger*, *Bacillus*, *Kluyveromyces*, *Candida*, *Mucor*, *Penicillium*, *Rhizopus*, *Saccharomyces*, *Sporotrichum*, *Trichoderma* and *Streptomyces*.

A further aspect of the invention concerns the provision of an aqueous solution of carbohydrate origin, particularly a starch hydrolysate, more particularly a wheat starch hydrolysate, which is substantially free from phospholipids.

The starch hydrolysate is particularly a hydrolysate derived from wheat starch, although hydrolysates from other starches, e.g., corn, waxy corn, potato, tapioca, rice, sorghum or waxy sorghum starch may be used if problems are encountered in filtering the hydrolysates and/or with the clarity of the filtrates. The starch hydrolysate which may be treated by the process of the invention may be a hydrolysate of any degree of hydrolysis, e.g., a 10-20 D.E. syrup (D.E.=dextrose equivalent), produced for example by treating a starch with an acid or with an alpha-amylase. This initial starch hydrolysate may be treated by the process of the invention and may at the same time or subsequently be submitted to additional enzymatic actions of known type to produce a range of starch hydrolysates or syrups of D.E.s in the range 20 to 100. The process of the invention is preferably carried out at a temperature of 20° to 110° C., more preferably 50° to 100° C. The pH of the starch hydrolysate is maintained preferably up to 8, particularly in the range 3.5 to 6.5. The time is that required to achieve the desired improvement in rate of filtration and/or filtrate clarity and may be between 1 hour and 5 days depending upon the enzyme dosage, the nature of the substrate used and the product desired.

In addition to improving the filterability of the starch hydrolysate and the clarity of the filtrate produced, the process according to the invention reduces foaming of the hydrolysate and makes the filtrate more susceptible to further purification steps, e.g., by ion-exchange and for carbon treatment.

The invention will now be further described with reference to the following examples in which enzyme determinations were carried out by the following methods:

(a) Phospholipase L Estimation 0.25 ml of a 20 millimolar aqueous solution of lysolecithin (e.g., that sold by the Sigma Company under product No. L 4129, approximately 99% and containing primarily palmitic and stearic acids) is mixed with 0.25 ml acetate buffer (pH 4.5, 0.02 M) and held in a thermostat at 55° C. for approximately 5 minutes.

50 microliter of an enzyme sample (appropriately diluted with water) is then added.

Exactly 1 minute after addition of the enzyme, 25 microliter of the incubation mixture is mixed with 0.25 ml "Enzyme Reagent 1" and incubated for 5 minutes at 37° C. Subsequently, 0.5 ml "Enzyme Reagent 2" is added followed by a further incubation for 5 minutes at 37° C.

The optical density (O.D.) of the purple-colored solution is read at 555 nm.

The test is repeated but the enzyme and substrate are incubated for 10 minutes instead of for 1 minute.

The difference between the two O.D. values yields: $\Delta$O.D. for the difference between the 1- and 10-minute incubation periods. Dividing $\Delta$O.D. by 9 gives the $\Delta$O.D. for 1 minute.

"Enzyme Reagent 1" and "Enzyme Reagent 2" refer to a commercial method for nonesterified fatty acid determination (NEFA QUICK "BMY") marketed by Boehringer Mannheim Yamanouchi K.K.

The estimation of the free fatty acid figure is made using a calibration curve obtained by applying the NEFA QUICK "BMY" test to standard oleic acid solutions.

The number of micromoles of free fatty acid liberated per minute is equivalent to the number of units of phospholipase present in the 50-microliter enzyme sample. The number of units per gram of protein in the enzyme composition may then be calculated.

(b) Phospholipase C Estimation

The method used was that described by Mannheim Boehringer (Catalogue No. 15636) which involves hydrolysing a standard solution of lecithin and estimating optically the glycerol produced.

(c) Xylanase and Beta-Glucanase Estimation

This test determines the rate at which the enzyme composition under test liberates D-xylose and D-glucose respectively, from standard xylan and beta-glucan solutions.

One ml solution of xylan (1%, w/v, Sigma Company No. X-3875) or beta-glucan (1%, w/v, Sigma Company No. G-6513) in an acetate buffer of pH 4.5, 0.01 M is mixed with 100 microliter of the enzyme solution under test, suitably diluted with water. Before mixing, the substrate solution is held in a thermostat at 55° C. for about 10 minutes. Incubation of the enzyme/substrate mixture is carried out at 55° C. After 5 and 10 minutes respectively, 0.5 ml of the incubation mixture is mixed with 0.5 ml DNS (dinitrosalicylic acid) reagent and following completion of the sampling, the samples (incubation mixture+DNS) are heated in boiling water for 10 minutes, 2.5 ml of water added and the final mixture cooled. The optical density (O.D.) is measured at 540 nm at room temperature.

The substrate blank value is determined by mixing 1 ml substrate solution with 100 microliter water, incubating for 10 minutes at 55° C., mixing 0.5 ml of this solution with 0.5 ml DNS-reagent and following the test procedure described above. At the dilutions used, the enzyme blank value is negligible.

From the linear portion of the graph of optical density against time the rate of change of O.D. per minute is calculated. Calibration curves established for D-xylose and D-glucose under the above conditions are used to estimate the amount of D-xylose/D-glucose released by the enzyme composition under test.

As 1 unit xylanase or beta-glucanase is the amount of enzyme, releasing under the described conditions per minute 1 micromole product, measured as D-xylose/D-glucose, the number of units of enzyme in the sample may be calculated.

(d) Protein Estimation

The method used was that described by Lowry, et al, *J. Biol. Chem.*, 193, pp 265–275 (1951).

EXAMPLE 1

Preparation of an Enzyme Composition According to the Invention

The enzyme composition was prepared from a commercially available beta-glucanase preparation, FINIZYM 200 L, Batch KZN0015, sold by Novo Industri A/S. FINIZYM 200 L is a fungal beta-glucanase preparation produced by submerged fermentation of a selected strain of *Aspergillus niger*. The enzyme composition is said to hydrolyse barley beta-glucans (1,4-beta-1,3-beta-glucans) into oligosaccharides and glucose and finds use during fermentation and storage of beer to prevent filtration difficulties and to prevent precipitation of beta-glucans.

Thirty ml of FINIZYM 200 L, Batch KZN0015, were diluted with 30 ml of demineralised water. This mixture was centrifuged for 5 minutes at 3500 r.p.m. to remove solid particles. Fifty ml of the supernatant liquor was separated chromatographically on a semi-analytical BIO-RAD polyacrylamide Bio-gel P-60 (100–200 mesh) column (diameter 5 cm and height 23 cm), eluted with an acetic acid buffer at pH 5.2 and collected in 10-ml fractions. The chromatogram had two distinct absorbance peaks at 280 nm corresponding to protein absorbance. The fractions corresponding to the two peaks were tested for phospholipase L activity using a lysolecithin substrate as described earlier in this specification. The fractions (16 to 40) corresponding to the first peak contained the phospholipase L activity and were bulked The bulked fractions were next concentrated on an AMICON DIAFLO XM-50 ultrafilter and then the concentrate chromatographed on a semi-analytical BIO-RAD polyacrylamide Bio-gel P-150 (50-150 mesh) column (diameter 5 cm, height 90 cm), eluted with an acetic acid buffer at a pH 5.2 into 10-ml fractions. The chromatogram had five distinct peaks and the fractions corresponding to the peaks were tested for phospholipase L activity as described above. The fractions showing the activity (59 to 72) were bulked and concentrated on an AMICON DIAFLO XM-50 ultrafilter.

The concentrate was in turn fractionated on a semi-analytical PHARMACIA fast flow DEAE-Sepharose anion-exchange column (diameter 5 cm, height 33 cm), eluted with a piperazine-HCl buffer at pH 5.2 applying a linearly increasing sodium chloride gradient and taking 10-ml fractions. The chromatogram had six distinct peaks. The fractions with phospholipase L activity (55 to 63) were again bulked and concentrated on an AMICON DIAFLO XM-50 ultrafilter and then desalted by means of a PHARMACIA Sephadex G-25M column PD-10.

The desalted concentrate was next fractionated on an analytical PHARMACIA MONO Q anion-exchange column (diameter 5 mm, length 50 mm) eluted with a diethanolamine buffer at pH 9.4 applying a stepwise increasing sodium chloride gradient and collecting 2-ml fractions. The chromatogram had seven distinct peaks and the fractions representing two peaks, namely, fractions 16 to 19 and 21 to 25, were found to contain the phospholipase L activity, the 16 to 19 fractions when bulked having 80 times more activity than the bulked 21 to 25 fractions. After three such operations and bulking of the 16 to 19 fractions followed by concentration on an AMICON MINICON-B concentrator, a solution was obtained containing 0.4292 mg protein/ml which had a phospholipase L activity of 422,000 units/gram protein and a ratio of phospholipase:xylanase and beta-glucanase of more than 500:1.

EXAMPLE 2

Preparation of an Enzyme Composition According to the Invention

The apparatus consisted of a fermentor of total volume 2 liter (working volume 1.4 liter) which was held in a thermostat at 30° C. and was aerated by compressed air at 0.7 l air per liter broth per minute.

The fermentation medium comprised 20 g/l PROFLO (cottonseed flour), 20 g/l commercial corn-oil, 1 g/l ammonium sulphate, 1 g/l potassium dihydrogen phosphate, 0.5 g/l hydrated magnesium sulphate, 0.5 g/l potassium chloride, 5 mg/l hydrated ferrous sulphate, 1.6 mg/l hydrated manganese sulphate, 1.4 mg/l hydrated zinc sulphate and 2 mg/l hydrated cobalt chloride, which were dissolved or suspended in a potassium hydrogen phthalate/sodium hydroxide buffer (0.05 M potassium hydrogen phthalate pH=5). The contents of potassium hydrogen phthalate and sodium hydroxide in the final medium were 9.5 g/l and 1.15 g/l respectively.

Preparation of the Seed Culture

Aspergillus niger (ATCC 13496) was grown from spores as a seed culture on a medium comprising 2 g/l dextrose, 1 g/l ammonium sulphate, 1 g/l potassium dihydrogen phosphate, 0.5 g/l hydrated magnesium sulphate, 0.5 g/l potassium chloride, 0.1 g/l yeast extract, 5 mg/l hydrated ferrous sulphate, 1.6 mg/l hydrated manganese sulphate, 1.4 mg/l hydrated zinc sulphate and 2 mg/l hydrated cobalt chloride. The seed culture was grown at 30° C. on a total volume of 50 ml medium in a 500 ml shaken flask in a shaken waterbath for 4 days.

The fermentation medium was inoculated with 100 ml seed culture. The temperature was 30° C. and the air flow constant. The rotation speed of the impeller was 250 r.p.m. for the first 48 hours and the speed was then increased by 100 r.p.m. per 24 hours. After 6 days, the speed was increased to 750 r.p.m. and held constant until the end of the fermentation. The fermentation time was 12 days. The biomass was not quantified; pH dropped slightly to reach pH 4.9 after 12 days. The phospholipase L activity in the cell-free medium was measured with the NEFA Quick Test described above. After removal of the mycelium by filtration, 800 ml liquid was recovered (during the fermentation, the volume decreased due to evaporation of water). The 800 ml liquid contained 137 phospholipase L units per ml. A total of 109,600 units was thus recovered from the fermentation by ultrafiltration.

Further analysis revealed that the enzyme solution contained 178,195 units phospholipase L/gram protein, 8182 units xylanase/gram protein and 1494 units beta-glucanase/gram protein, i.e., a ratio of phospholipase:xylanase and beta-glucanase of 18:1.

EXAMPLE 3

Evaluation of the Product of Example 1 in the Clarification of a Wheat Starch Hydrolysate A 35% d.s. by weight slurry of wheat "A" starch in water was continuously converted to an 18 D.E. maltodextrin, using a conventional alpha-amylase hydrolysis process.

After adjustment of the pH to 4.8 and the temperature to 55° C., 0.15% by weight calculated on dry basis of malt extract, 400° L (beta-amylase) was added to a 2-liter batch of the 18 D.E. maltodextrin. The mixture was allowed to incubate for 20 hours and when the D.E. had risen to 42, the filtration rate of the syrup was determined using a laboratory, vacuum precoat filter which had been shown to give results correlating with an industrial, rotary vacuum precoat filter. The filtration was carried out at a syrup temperature of 60° C. after an adjustment of the pH to 4.8.

Two incubations were carried out. The first included no additive and a filtration rate of 120 $l \cdot h^{-1} \cdot m^{-2}$ was obtained. The second incubation was carried out with the addition of 0.1% by weight calculated on a dry basis of the concentrated 16 to 19 bulked fractions described in Example 1. The filtration rate in this instance was 500 $l \cdot h^{-1} \cdot m^{-2}$.

EXAMPLE 4

Evaluation of the Product of Example 2 in the Production of a Wheat Starch Hydrolysate A 10-20 D.E. maltodextrin was saccharified at pH 5.2 and at 58° C. to a high maltose syrup using a beta-amylase enzyme. The product had a filtration rate of 104 $l \cdot h^{-1} \cdot m^{-2}$ and, after carbon refining, a clarity of 94 units and a color of 11.6 units, both clarity and color being obtained by optical density measurements. When the saccharification product was pretreated with 0.5 units/gram maltodextrin of the enzyme of Example 2, the filtration rate was 323 $l \cdot h^{-1} \cdot m^{-2}$ and the clarity and color after carbon refining were 100 and 0.8 respectively.

What is claimed is:

1. A process for the treatment of an aqueous solution of a wheat starch hydrolysate which is difficult of filter and/or which produces a cloudy filtrate and which contains as an impurity a phospholipid which comprises incubating said wheat starch hydrolysate with an enzyme composition comprising a phospholipase, a xylanase and a beta-glucanase enzyme at a temperature of 20° C. to 110° C. and a pH maintained up to 8 for a sufficient time to achieve a desired filtration rate and/or filtrate clarity, the ratio of phospholipase enzyme to total xylanase and beta-glucanase enzymes in the enzyme composition being at least 0.05:1.

2. A process according to claim 1 wherein the enzyme composition contains a phospholipase and a xylanase and/or beta-glucanase in which the ratio of phospholipase to total xylanase and beta-glucanase lies in the range of 0.05:1 to 50:1.

3. A process according to claim 1 wherein the enzyme composition used in the process contains at least 5000 units phospholipase/gram total protein.

4. A process according to claim 1 wherein the phospholipase enzyme has $L_1$, $L_2$ or C activity.

5. A process according to claim 1 wherein the ratio of phospholipase enzyme to total xylanase and beta-glucanase enzymes in the enzyme composition is at least 10:1.

6. A process according to claim 2 wherein the ratio of phospholipase to total xylanase and beta-glucanase lies in the range 1:1 to 30:1.

7. A process according to claim 3 wherein the enzyme composition contains at least 15,000 units phospholipase/gram total protein.

8. A process according to claim 3 wherein the enzyme composition contains at least 15,000 units phospholipase/gram total protein.

9. A process according to claim 3 wherein the enzyme composition contains at least 100,000 units phospholipase/gram total protein.

10. A process according to claim 1 which is carried out at a temperature of 50° to 100° C.

11. A process according to claim 1 wherein the pH is maintained in the range of 3.5 to 6.5.

* * * * *